(12) United States Patent
Hasenzahl et al.

(10) Patent No.: US 6,849,570 B2
(45) Date of Patent: Feb. 1, 2005

(54) PROCESS FOR THE PRODUCTION OF A TITANIUM SILICALITE SHAPED BODY

(75) Inventors: Steffen Hasenzahl, Meintal (DE); Ralf Jantke, Mömbris (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/204,305

(22) PCT Filed: Mar. 21, 2001

(86) PCT No.: PCT/EP01/03227
§ 371 (c)(1),
(2), (4) Date: Oct. 15, 2002

(87) PCT Pub. No.: WO01/72419
PCT Pub. Date: Oct. 4, 2001

(65) Prior Publication Data
US 2003/0078160 A1 Apr. 24, 2003

(30) Foreign Application Priority Data
Mar. 29, 2000 (EP) .......................................... 00106671

(51) Int. Cl.$^7$ ............................. B01J 21/08; B01J 29/06; B01J 27/198; B01J 27/182; C07C 249/00
(52) U.S. Cl. ........................... 502/242; 502/64; 502/71; 502/208; 502/214; 264/628; 264/638; 264/656; 564/253; 564/265; 564/266; 564/267; 564/268
(58) Field of Search ................................. 502/202, 208, 502/214, 242; 264/628, 636, 638; 549/523, 524, 531; 564/253, 265–268

(56) References Cited

U.S. PATENT DOCUMENTS

| | | | | |
|---|---|---|---|---|
| 4,794,198 | A | * 12/1988 | Roffia et al. ................. | 564/267 |
| 5,525,563 | A | 6/1996 | Thiele et al. | |
| 5,527,520 | A | * 6/1996 | Saxton et al. ............... | 423/706 |
| 5,637,715 | A | 6/1997 | Thiele et al. | |
| 5,756,778 | A | 5/1998 | Thiele et al. | |
| 5,869,706 | A | * 2/1999 | Dartt et al. .................. | 549/531 |
| 5,885,546 | A | 3/1999 | Kumar et al. | |
| 5,919,430 | A | 7/1999 | Hasenzahl et al. | |
| 6,008,389 | A | * 12/1999 | Grosch et al. .............. | 549/533 |
| 6,054,112 | A | 4/2000 | Hasenzahl et al. | |
| 6,106,803 | A | 8/2000 | Hasenzahl et al. | |
| 6,380,119 | B1 | * 4/2002 | Grosch et al. ................. | 502/49 |
| 6,491,861 | B1 | * 12/2002 | Grosch et al. .............. | 264/628 |
| 6,551,546 | B1 | * 4/2003 | Grosch et al. .............. | 264/621 |
| 6,603,027 | B1 | * 8/2003 | Catinat et al. .............. | 549/533 |
| 2001/0055562 | A1 | * 12/2001 | Hasenzahl et al. .......... | 423/700 |
| 2002/0091277 | A1 | * 7/2002 | Strebelle et al. ............ | 549/532 |
| 2003/0073856 | A1 | * 4/2003 | Hancu et al. ................ | 549/533 |
| 2003/0083510 | A1 | * 5/2003 | Haas et al. .................. | 549/531 |
| 2003/0158431 | A1 | * 8/2003 | Balthasart ................... | 549/531 |

FOREIGN PATENT DOCUMENTS

| | | |
|---|---|---|
| BE | 1001038 | 3/1990 |
| DE | 19623611 | 12/1997 |
| DE | 196 23 972 | 12/1997 |
| DE | 198 39 792 | 3/2000 |
| EP | 0325053 | 7/1989 |
| EP | 0 791 558 | 8/1997 |
| EP | 0 906 784 | 4/1999 |
| FR | 2 471 950 | 6/1981 |
| WO | WO 9928030 | 6/1999 |
| WO | WO 9952626 | 10/1999 |

OTHER PUBLICATIONS

Thangaraj, A. et al., "Studies on the Synthesis of Titanium Silicalite, TS–1," Zeolites, 1992, pp. 943–950, vol. 12, Nov./Dec. issue, Butterworth–Heinemann, USA, 8 pages, no month available.

Thangaraj, A. et al., "Catalytic Properties of Crystalline Titanium Silicalites," Journal of Catalysis, 1991, pp. 1–8, vol. 130, Academic Press, Inc., USA, 8 pages, no month available.

Zhang, G. et al., "Preparation Of Colloidal Suspensions Of Discrete Ts–1 Crystals," Chemistry of Materials, 1997, pp. 210–217, vol. 9, No. 1, American Chemical Society, Washington, D.C., USA, 8 pages.

* cited by examiner

Primary Examiner—Mark L. Bell
Assistant Examiner—Patricia L. Hailey
(74) Attorney, Agent, or Firm—Smith, Gambrell & Russell, LLP

(57) ABSTRACT

The present invention relates to a process for the production of a titanium silicalite shaped body by: (a) forming a formable composition containing titanium silicalite, a binder and a pasting agent, so that the Curd curve of the formable composition has a plateau value in the range from 20 to 90 mm; (b) shaping the composition of step (a) to form a green body; (c) optionally drying and (d) calcining the green body, to a titanium silicalite shaped body obtainable by that process, and to the use of such titanium silicalite shaped bodies in the epoxidation of olefins or the ammoximation of ketones.

15 Claims, No Drawings

PROCESS FOR THE PRODUCTION OF A TITANIUM SILICALITE SHAPED BODY

The present invention relates to a process for the production of a titanium silicalite shaped body, to a titanium silicalite shaped body obtainable by the above-described process, and to processes for the epoxidation of olefins and for the ammoximation of ketones using such a titanium silicalite shaped body.

U.S. Pat. No. 4,410,501 discloses a process for the preparation of titanium silicalite and also the use of the titanium silicalite so prepared as catalyst in a number of reactions, including oxidation reactions. The titanium silicalite is prepared by forming a synthesis gel, starting from a hydrolyzable silicon compound, such as, for example, tetraethyl orthosilicate, and a hydrolyzable titanium compound, by addition of tetra-n-propylammonium hydroxide, hydrolyzing and crystallizing that reaction mixture. When the crystallization is complete, the crystals are separated off by filtration, washed, dried and finally calcined for 6 hours at 550° C.

DE-A 197 31 672 describes a process for the preparation of titanium silicalite granules, according to which a synthesis gel containing an $SiO_2$ source, a $TiO_2$ source, a compound containing tetra-n-propylammonium ions, a base and water is crystallized under hydrothermal conditions and the titanium silicalite suspension so formed is subjected, without being separated off beforehand, to spray-drying or to fluidised bed granulation drying, and the resulting titanium silicalite granules are then calcined at a temperature of from 400° C. to 1000° C., preferably from 500° C. to 750° C.

Especially when using the catalyst in a fixed bed in the epoxidation of olefins or in the ammoximation of ketones, it is worthwhile to form relatively large shaped bodies which have adequate hardness and abrasion resistance, so that the physical integrity of the catalyst shaped bodies is maintained even after a relatively long operating period. In particular, the formation of fine grain, which is discharged with the reaction product, which on the one hand leads to losses of catalyst and on the other hand makes necessary more complicated separation of the reaction products, is to be reduced or avoided.

DE-A 196 23 611 discloses a process for the production of titanium silicalite shaped bodies according to which a synthesis gel is first prepared by hydrolysis of a silicon source, a titanium source and tetrapropylammonium hydroxide, the synthesis gel is crystallized under hydrothermal conditions, and the resulting solid is separated off, for example by centrifugation, dried and then calcined at 550° C. The calcined titanium silicalite powder is then processed further to a plastic composition by the addition of water, binders, such as, for example, silica sol, and plasticisers, such as methylcellulose; the plastic composition is extruded to strands, which are dried and again calcined at 500° C. for 5 hours. The strands are then comminuted to granules or grit having a particle size of from 1 to 10 mm.

WO 98/55229 discloses a comparable process in which the formable composition is prepared by addition of a mixture of water and alcohol as pasting agent.

Despite those processes known from the prior art for the production of titanium silicalite shaped bodies, there is a continued need in the industry to modify such processes in order to obtain shaped bodies having improved mechanical properties. Accordingly, the object of the present invention is to provide a process for the production of titanium silicalite shaped bodies which yields shaped bodies having improved mechanical properties. A further object of the present invention is to provide a titanium silicalite shaped body having improved properties, which can be used as catalyst also in epoxidation reactions of olefins and in ammoximation reactions of ketones.

That object is achieved by a process for the production of a titanium silicalite body by a) forming a formable composition containing titanium silicalite, one or more binders, so that the Curd curve of the formable composition has a plateau value in the range from 20 to 90 mm, b) shaping the composition of step a) to form a green body, c) optionally drying and d) calcining the green body, and by a titanium silicalite shaped body obtainable by that process.

Surprisingly, it has been found that, if the formable composition is so formed that its Curd curve has a plateau value in the range from 20 to 90 mm, the resulting titanium silicalite bodies have improved mechanical properties, such as, for example, higher fracture resistance.

The plateau value in the Curd curve of the formable composition is dependent under given measuring conditions on a large number of different factors such as, for example, the grain size of the titanium silicalite crystals used, the nature and amount of the binder, the nature and amount of the pasting agent, where present, the nature and amount of shaping auxiliaries, etc. Accordingly it is not possible to indicate for all those factors precise ranges within which a plateau value of the Curd curve in the range according to the invention is achieved.

However, a person skilled in the art who is familiar with the above-mentioned factors affecting the plateau value of the Curd curve is readily able to determine, by means of simple standard tests, how the individual factors must be selected in order to yield the Curd value according to the invention.

The measuring method for plotting the Curd curve and determination of the plateau value from the Curd curve is described in detail in the operating instructions for the Curd Meter model M-301AR from "Iio Electric Co., Ltd., 2-23-2, (1140) YOYOGI, SHIBUYA-KU, TOKYO, Japan".

Especially suitable titanium silicalite shaped bodies having high lateral fracture resistance are obtained when the formable composition has a plateau value of the Curd curve in the range from 30 to 70 mm.

The titanium silicalite bodies according to the invention are especially suitable as catalysts in fixed-bed reactors for the oxidation of organic compounds, especially for the epoxidation of olefins and the ammoximation of ketones.

The titanium silicalite used to form the formable composition in accordance with the process of the invention may be prepared by conventional processes known from the prior art. To that end, an $SiO_2$ source, a $TiO_2$ source, a template compound and water are combined. hydrolyzable silicon compounds and hydrolyzable titanium compounds are especially suitable as the starting material, which are then hydrolyzed in the presence of water. Suitable hydrolyzable silicon and titanium compounds are tetraalkyl orthosilicates and tetraalkyl orthotitanates, with alkyl preferably being selected from the group consisting of methyl, ethyl, propyl and butyl. The most preferred starting materials are tetraethyl orthosilicate and tetraethyl orthotitanate. Template compounds are to be understood as being compounds which determine the crystal structure by being taken up into the crystal lattice of the product during crystallization. Preferred template compounds are quaternary ammonium compounds, such as tetraalkylammonium compounds, especially tetraalkylammonium hydroxide, such as tetra-n-propylammonium hydroxide for the preparation of titanium silicalite-1 (MFI structure), tetra-n-butylammonium hydroxide for the preparation of titanium silicalite-2 (MEL structure) and tetraethylammonium hydroxide for the preparation of titanium-β-zeolite (DEA crystal structure).

The synthesis gel pH value of >9, preferably >11, which is necessary for the synthesis is adjusted by the quarternary ammonium compound used as the template compound, which has a basic reaction. The temperature at which the synthesis gel is prepared may be varied within wide limits, but it is preferred to cool the mixture of silicon source and titanium source to a temperature in the range of from 0° C. to 10° C., preferably from 0° C. to 5° C., especially 1° C., and then add the template compound in aqueous solution, which has been cooled to the same temperature.

In a further embodiment of the present invention, when tetraalkyl orthosilicates and tetraalkyl orthotitanates are used as the silicon source and the titanium source, respectively, the synthesis gel is heated at a temperature of from 75° C. to 95° C. for a period of from 120 to 200 minutes, and the resulting alcohol is distilled off as an azeotropic mixture with water, in order to support the hydrolysis of the hydroysable titanium and silicon compounds. The synthesis gel is then crystallized, optionally after an additional aging time, at a temperature of from 150° C. to 220° C., preferably from 170° C. to 190° C., under autogenous pressure. Under the specified conditions, the crystallization time is generally less than 3 days, preferably less than 24 hours.

Silicon/titanium mixed oxides, which can be prepared, for example, by flame hydrolysis of a mixture of $SiCl_4$ and $TiCl_4$, are also highly suitable starting materials. They may be dispersed in a suitable solution containing template and base and be crystallized as described above, after an optional aging step or the addition of seed crystals.

The titanium silicalite suspension so obtained may be processed further by various methods. On the one hand it is possible to separate the titanium silicalite crystals from the mother liquor by conventional solid/liquid separation processes, such as centrifugation and filtration, and dry and calcine them. Alternatively, the titanium silicalite solid may be obtained by spray-drying or by means of fluidised bed granulation drying with or without subsequent calcination. According to a further embodiment, the crystallite suspension may optionally be concentrated by condensation, for example by evaporating off readily volatile constituents or by addition of titanium silicalite solid. The titanium silicalite suspension may then be mixed directly with a binder and, if necessary, a pasting agent and further auxiliary substances in order to prepare the formable composition according to the process of the invention.

After drying, the titanium silicalite solid or the concentrated titanium silicalite suspension is processed to a formable composition with one or more binders, optionally with shaping auxiliaries and, optionally, a pasting agent. Suitable binders are in principle all substances known for such purposes. Preference is given to the use of oxides of silicon, aluminum, boron, phosphorus, titanium, zirconium and/or magnesium or corresponding precursors. Especially preferred binders are silicon dioxides, aluminum oxides, titanium oxides and clay minerals and mixtures thereof. Examples of silicon dioxides and silicon dioxide precursors are precipitated or fumed silicas, silica sols, tetraalkoxysilanes, partially condensed silicic acid esters and polysiloxanes, an example of aluminum oxide is (pseudo) boehmite, examples of titanium dioxide are anatase or brookite, and examples of clay minerals are montmorillonites, kaolins, bentonites and sepiolites.

The binders may be used as powders or in the form of sols, suspensions or solutions. The amount of binder is generally from 1 to 99 wt. %, preferably from 5 to 60 wt. % and especially from 10 to 40 wt. %, based on the solids content of the formable composition.

Very especially suitable binders are aluminum oxides, polysiloxanes, silica sols, clay minerals and the combination of $SiO_2$ and boron compounds. It has been found that titanium silicalite shaped bodies having outstanding mechanical properties, especially a high fracture resistance, are obtained especially when aluminum oxide, a clay mineral or a combination of silica sol and a boron compound is used, even if particular plateau values of the Curd curve are not maintained in the preparation of the formable composition. Special preference is given to a mixture of silica sol and a boron compound as binder for the production of titanium silicalite shaped bodies. Boric acid is especially suitable as the boron compound. In that preferred mixture of silica sol and a boron compound, the silica sol is present in an amount of from 50 to 99.99 wt. %, based on the total mass of silica sol and boron compound.

There may be added as shaping auxiliaries substances that primarily promote the formation of a plastic composition during the kneading shaping and drying step and, moreover, have an advantageous effect on the mechanical stability of the shaped body during shaping and drying. Such substances are preferably removed when the green body is calcined. Preference is given to organic viscosity-increasing substances, such as, for example, cellulose, starch, acrylate, polyacrylate, polymethacrylate, polyvinyl alcohol, polyvinylpyrrolidone, polyisobutene and polytetrahydrofuran, polyglycol ethers, fatty acid compounds and/or wax emulsions.

Bases or acids may be added as further additives. There are suitable, for example, ammonia, amines or quaternary ammonium salts, as well as carboxylic acids, such as, for example, formic, acetic or propionic acid. Of course, mixtures of two or more of the above-mentioned additives may also be used.

Pore-forming substances, such as polyalcohols, fructose, pentaerythritol, cellulose or sawdust, may be used as further additives. Such substances burn out during the calcination and leave behind additional meso- and macro-pores in the shaped body.

When a twin-screw extruder is used, the components may be mixed immediately prior to the extrusion. Shaping auxiliaries are used in the process according to the invention in an amount of from 0 to 40 wt. %, preferably from 1 to 10 wt. %, based on the solids content of the formable composition.

There is preferably used as pasting agent in the process according to the invention an aqueous medium optionally containing a water-miscible organic solvent. If the binder used is a metallic acid ester, such as, for example, alkyl orthosilicate or alkyl orthotitanate, it is preferred to use as pasting agent a mixture of water and an alcohol corresponding to the alcohol component of the metallic acid ester. When a mixture of alcohol and water is used as pasting agent, the alcohol content of the mixture is generally from 1 to 80 wt. %, preferably from 5 to 70 wt. % and especially from 10 to 60 wt. %, in each case based on the total weight of the mixture.

It is also possible to add to the formable composition any desired further components, such as, for example, further zeolites, fumed or precipitated oxides and metals, and, in order to improve the mechanical stability, inorganic fibres, such as, for example, Al—Si fibres and/or Ca—Si fibres.

The pasting agent is used in such amounts that a plastic extrudable composition is formed, preferably in such an amount that the solids content of the formable composition is from 10 to 90 wt. %, preferably from 60 to 80 wt. %.

The order in which the constituents of the formable composition are added depends on a number of factors and must be worked out for each case individually. It is possible to add to the titanium silicalite solid first the binder, then the shaping auxiliaries, if used, and finally the pasting agent. After the addition of the binder and, optionally, of the shaping auxiliary, the composition, which is generally still in powder form, is homogenised in a kneader, an extruder or a mixer, and then the pasting agent is added. The mixture so obtained is mixed until a plastic composition that can be formed into strands or extruded has formed. The operation is generally carried out at temperatures in the range from 10° C. to the boiling point of the pasting agent and under normal pressure, at a pressure slightly above atmospheric pressure or under a partial vacuum. The choice and the amounts of the substances used are to be matched so that the formable composition has a plateau value of the Curd curve in the range according to the invention.

In the case of the embodiment that starts from the concentrated titanium silicalite suspension, it is preferred to add the binder and, optionally, shaping auxiliaries to the titanium silicalite suspension and, if necessary in order to produce a kneadable composition, additionally to add a pasting agent.

All known mixing and shaping devices and processes may be used for the mixing and shaping. Such known shaping devices are described, for example, in Ullmann's Enzyklopädie der Technischen Chemie, 4th edition, Volume 2, page 295 ff, 1972. There are preferably used single- and twin-screw extruders or an extruding press. A large number of known geometric forms can be produced thereby, such as, for example, solid cylinders, hollow cylinders, stars, etc. However, the production of honeycomb bodies is also possible.

The green bodies so obtained, the diameter of which is from 1 to 10 mm, may subsequently be dried at room temperature or at elevated temperatures, optionally in the presence of water vapour.

The shaped bodies are then calcined in the presence of air, inert gas or oxygen at temperatures of up to 1100° C. The progression of the temperature with time, that is to say the heating rate, the times for which the intermediate and final temperatures are maintained, and the cooling rate, must be optimized for each case individually. The calcination may serve to remove the template and the additives from the green body and has a deciding influence on the mechanical stability, the pore volume or the specific surface area.

The resulting strands or extrudates may be comminuted. They are preferably comminuted to granules or grit having a particle diameter of from 0.1 to 5 mm, especially from 0.5 to 2 mm.

The Examples which follow serve to illustrate the present invention:

Apparatuses Used to Prepare the Formable Compositions

The formable compositions were prepared using 0.25 liter and 2.5 liter kneaders from Werner & Pfleiderer (type UK 0.25 and LUK 2.5), kept at a temperature of 10° C. by means of a thermostat. Both kneaders were equipped with sigma blades, the 2.5 liter kneader additionally having an adjustable discharge screw. formable compositions prepared in the 0.25 liter kneader were shaped by means of a hand extruder having a plate with 4 mm holes. Kneading compositions prepared in the 2.5 litre kneader having a discharge screw were extruded by means of the discharge screw (4 mm solid cylinder).

Characterization of the Formable Compositions

In order to characterize the formable compositions prior to shaping, the height of the plateau value of the Curd curve (plateau value) was determined. To that end, a sample vessel having a diameter of 50 mm and a height of 40 mm was filled completely with the formable composition to be studied. The formable composition was subjected to a pressure of 10 bar for 5 minutes by means of a press, in order to eliminate the effect of shear during the kneading.

The sample vessel was then placed onto the base plate of an M-301AR Curd meter from Iio Electric Col, Ltd. The base plate can be raised by means of an electric motor at a precisely adjustable speed. The measuring rod having a diameter of 2 mm, mounted on a precision spring (spring constant 6533 dyn/cm), was located directly above the center of the sample vessel. 400 g weights were additionally applied via the measuring rod.

The base plate with the sample vessel was then raised until the tip of the measuring rod was resting directly on the formable composition. The recording drum, likewise driven by the electric motor, with the recording paper mounted thereon was inserted and the recording stylus was adjusted with the aid of the zero point adjustment.

For the actual measurement, the base plate with the formable composition located thereon was raised at a constant rate of 0.36 cm/s. The progression of the height of the measuring rod with time was recorded on the synchronously rotating recording drum. At the start of the measurement, the measuring rod was raised with the formable composition until, after reaching a particular height, it was pressed into the kneading composition. Accordingly, the Curd curve first extends parallel to the plane diagonal, until it kinks and extends parallel to the x-axis. The distance from the x-axis, the height of the plateau of the Curd curve in mm (plateau value), was used to characterize the kneading composition.

Determination of the Lateral Fracture Resistance of the Calcined Shaped Bodies The lateral fracture resistance of the calcined shaped bodies was determined by means of a pellet fracture resistance tester (TBH 28 Erweka) by forming the mean value of a total of 20 measured values for each sample.

REFERENCE EXAMPLE 1

Preparation of Titanium Silicalite

Tetraethyl orthosilicate, tetraethyl orthotitanate and tetra-n-propylammonium hydroxide in aqueous solution were combined and hydrolysed in a 10 liter autoclave rendered inert with nitrogen. The amounts were so chosen that the molar ratio Si/Ti was 35, the molar ratio N/Si was 0.17 and the molar ratio $H_2O$/Si was 27. When the hydrolysis was complete and after distilling off the alcohol that had formed, which was replaced by the same volume of water, the synthesis gel was crystallized for 3 hours at 175° C. under hydrothermal conditions. The resulting solid was separated off, washed and dried overnight at 110° C. A portion of the dried product was additionally calcined at 550° C. for 4 hours in an atmosphere of air.

EXAMPLE 1

1027.6 g of calcined TS-1 powder from Reference Example 1, 26.0 g of methylhydroxycellulose (Tylose MH 1000, Hoechst) and 333.3 g of aluminium oxide (Plural SB, Condea) were weighed into a 2.5 liter kneader having a discharge screw; mixing was carried out for 10 minutes, and then 30.0 g of glacial acetic acid (Merck) were added. A total of 551.3 g of demineralised water was then added in the course of 20 minutes, during which there formed a compact composition, which was kneaded for a further 45 minutes.

The formable composition was characterised as described above. A plateau value of the Curd curve of 54 mm was obtained.

The formable composition was extruded by means of a discharge screw having a nozzle with a 4 mm bore. The resulting green bodies were dried using a Leister fan, left to stand in air overnight, and calcined at 550° C. for one hour in a chamber furnace (heating rate 100 k/h). The mean lateral fracture resistance of the shaped bodies was 87 N.

EXAMPLE 2

1800 g of dried TS-1 powder from Reference Example 1, 100 g of Tylose MH1000, 1360 g of Plural SB, 150 g of glacial acetic acid and 1880 g of demineralised water were placed in a 20 liter kneader and mixed for 15 minutes. In the course of 10 minutes, while kneading, a further 3000 g of TS-1 powder were added in portions and, after 10 minutes, 40 g of Zusoplast 126/3 (fatty acid preparation with non-ionic emulsifier, Zschimmmer & Schwarz) were added. The resulting composition was kneaded for a further 60 minutes.

The plateau value of the Curd curve of the formable composition was 81 mm. The formable composition was extruded as in Example 1. The lateral fracture resistance of the resulting shaped bodies was 46 N.

EXAMPLE 3

646.4 g of calcined TS-1 powder from Example 1, 32.0 g of Tylose MH1000 and 218.4 g of Plural SB were placed in a 2.5 litre kneader having a discharge screw and mixed for 10 minutes. A solution of 24.0 g of glacial acetic acid in 463.5 g of demineralised water was added to the mixture, and kneading was carried out for a further 60 minutes. There were then added to the composition, with further kneading, 6.4 g of Zusoplast 126/3 and, after a further 30 minutes, 20 g of petroleum.

The plateau value of the Curd curve of the formable composition was 59 mm. The formable composition was extruded as in Example 1. The lateral fracture resistance of the resulting shaped bodies was 103 N.

Comparison Example 1

102.8 g of calcined TS-1 powder from Example 1, 25 g of Plural SB, 2.8 g of glacial acetic acid and 2.5 g of Tylose MH1000 were placed in a 0.25 liter kneader and mixed for 10 minutes. There were then added thereto in portions, while kneading, 7.5 g of orthophosphoric acid (85 wt. %, Merck) and, in the course of 50 minutes, 67.1 g of water. In order to reduce the thixotropy of the composition, 11.8 g of ammonia solution (25 wt. %) were then added slowly.

The plateau value of the Curd curve of the formable composition was 94 mm. The formable composition was processed further as described in Example 1. The lateral fracture resistance of the shaped bodies was 7 N.

Comparison Example 2

120.1 g of dried TS-1 powder from Example 1, 34.7 g of Plural SB, 3.9 g of glacial acetic acid and 2.6 g of Tylose MH1000 were placed in a 0.25 liter kneader and mixed for 10 minutes. After the addition of 63.0 g of water, the resulting composition was kneaded for a further 30 minutes.

The plateau value of the Curd curve of the formable composition was 19 mm. The formable composition was processed further as described in Example 1. The lateral fracture resistance of the shaped bodies was 19 N.

A comparison of Examples 1-3 with Comparison Examples 1 and 2, all of which use aluminium oxide as binder, clearly shows that the lateral fracture resistance of the resulting calcined shaped bodies is dependent to a large extent on the plastic properties of the formable composition, and shaped bodies having a high lateral fracture resistance are obtained from formable compositions having a plateau value of the Curd curve in the range according to the invention.

EXAMPLE 4

3610.6 g of tetraethyl orthosilicate were placed in a 10 liter reactor and cooled to 1° C. A mixture of 3151.1 g of an aqueous tetra-n-propylammonium hydroxide solution (40 wt. %, Sachen) and 1229.3 g of deionised water was added in the course of 4 hours, with stirring. The reaction mixture was then heated to a maximum of 95° C. in order to distill off 5140 ml of a water/ethanol azeotropic mixture (TPA silicate solution).

102.75 g of calcined TS-1 powder from Reference Example 1 and 2 g of Tylose MH1000 were placed in a 0.25 liter kneader, and 128.2 g of the TPA silicate solution prepared above were added thereto. After mixing for 10 minutes, 4.2 g of glacial acetic acid and then 6.3 g of water were added dropwise.

The plateau value of the Curd curve of the formable composition was 33 mm. The formable composition was extruded by means of a hand extruder having a plate with 4 mm holes. The green bodies were processed further as described in Example 1. The lateral fracture resistance of the resulting shaped bodies was 32 N.

Comparison Example 3

For the preparation of a formable composition, 119.05 g of dried TS-1 powder from Example 1 and 2 g of Tylose MH1000 were placed in a 0.25 liter kneader, and 128.2 g of the TPA silicate solution prepared as in Example 4 were added. After mixing for 10 minutes, 9.0 g of ammonium acetate were added, and the resulting formable composition was kneaded for a further 20 minutes.

The plateau value of the Curd curve of the formable composition was 18 mm. The formable composition was extruded by means of a hand extruder having a plate with 4 mm holes. The green bodies were processed further as described in Example 1. The lateral fracture resistance of the calcined shaped body was so low that it could not be measured.

Comparison Example 4

822 g of calcined TS-1 powder from Example 1, 16.0 g of Tylose MH1000 and 1025.8 g of the TPA silicate solution prepared as in Example 4 were mixed in a 2.5 litre kneader having a discharge screw. A total of 28.4 g of glacial acetic acid was then added slowly in the course of 2 hours, while kneading.

The plateau value of the Curd curve of the formable composition was 14 mm. The formable composition was extruded by means of the kneader having a discharge screw.

The green bodies were processed further as described above. The lateral fracture resistance of the resulting shaped bodies was 10 N.

EXAMPLE 5

102.75 g of calcined TS-1 powder from Reference Example 1 and 2 g of Tylose MH1000 were placed in a 0.25 litre kneader and mixed with 62.5 g of silica sol Ludox AS40. 49.7 g of water and 1.8 g of ammonia solution (25 wt. %) were then added. The resulting composition was kneaded for a total of 2 hours.

The plateau value of the Curd curve of the formable composition was 37 mm. The formable composition was extruded by means of a hand extruder having a plate with 4 mm holes. The green bodies were processed further as described in Example 1. The lateral fracture resistance of the resulting shaped bodies was 21 N.

Comparison Example 5

119.05 g of dried TS-1 powder from Example 1 and 2 g of Tylose MH1000 were placed in a 0.25 liter kneader and mixed with 62.5 g of silica sol Ludox AS40. After the addition of 18.6 g of water, the resulting composition was kneaded for a total of 40 minutes.

The plateau value of the Curd curve of the formable composition was 14 mm. The formable composition was extruded by means of a hand extruder having a plate with 4 mm holes. The green bodies were processed further as described in Example 1. The lateral fracture resistance of the resulting shaped bodies was 15 N.

EXAMPLE 6

1063.3 g of calcined TS-1 powder from Example 1, 26.0 g of Tylose MH1000 and 618.8 g of silica sol Ludox AS40 were placed in a 2.5 litre kneader having a discharge screw and mixed for 10 minutes. 200 g of water and 16.5 g of ammonia solution (25 wt. %) were then added. The resulting composition was then kneaded for a further 3 hours.

The plateau value of the Curd curve of the formable composition was 67 mm. The formable composition was extruded by means of the discharge screw. The green bodies were processed further as described in example 1. The lateral fracture resistance of the resulting shaped bodies was 21 N.

EXAMPLE 7

102.8 g of calcined TS-1 powder from Example 1, 11.1 g of boric acid (99.5%, Merck), 2.0 g of Tylose MH1500 (Hoechst) and 46.9 g of silica sol Ludox AS40 (DuPont) were weighed into a 0.25 litre kneader and mixed. In the course of one hour, during the mixing, 3.0 g of aqueous ammonia solution (25 wt. %) and 42.5 g of water were added in portions. The resulting composition was then kneaded for a further 10 minutes.

The plateau value of the Curd curve of the formable composition was 45 mm. The formable composition was extruded by means of a hand extruder having a plate with 4 mm holes. The green bodies were processed further as described in Example 1. The mean lateral fracture resistance of the resulting shaped bodies was 57 N.

A comparison of Example 5 and Example 7 shows that comparable total amounts of binders and amounts of the other constituents lead to similar plateau values of the Curd curve, but the addition of boric acid as a binder component additionally brings about a marked increase in the lateral fracture resistance of the resulting shaped body. Furthermore, a comparison of the Examples according to the present invention clearly shows that the use of aluminum oxide and of the combination of silica sol and a boron compound as binder leads to the highest values for the lateral fracture resistance of the resulting shaped bodies.

What is claimed is:

1. Process for the production of a titanium silicalite shaped body by
   (a) forming a formable composition containing titanium silicalite, a binder and a pasting agent, so that the Curd curve of the formable composition has a plateau value in the range from 20 to 90 mm,
   (b) shaping the composition of step a) to form a green body,
   (c) optionally drying and
   (d) calcining the green body.

2. Process according to claim 1, wherein
the Curd curve of the formable composition has a plateau value in the range from 25 to 70 mm.

3. Process according to any one of the preceding claim 1, wherein
compounds of silicon, aluminum, boron, phosphorus, zirconium and/or titanium are used as binder.

4. Process according to claim 3, wherein
the binder is selected from aluminum oxide, silicon dioxide, hydrolyzable silicon compounds and partial or complete hydrolysates thereof, boron compounds, phosphorus compounds, clay minerals and mixtures thereof.

5. Process according to claim 4, wherein
the binder contains aluminium oxide.

6. Process according to claim 4, wherein
the binder contains a clay mineral.

7. Process according to claim 4, wherein
the binder contains a combination of silica sol and a boron compound.

8. Process according to claim 7, wherein
the boron compound is boric acid.

9. Process according to claim 7, wherein
silica sol is present in the mixture of silica sol and a boron compound in an amount of from 50 to 99.99 wt. %.

10. Process according to claim 1, wherein
the pasting agent used is an aqueous medium optionally containing a water-miscible organic solvent.

11. Process according to claim 1, wherein
the green body is calcined at a temperature of from 400° C. to 1000° C.

12. Process according to claim 11, wherein
the green body is calcined at a temperature from 500° C. to 750° C.

13. A titanium silicalite shaped body resulting from a process according to claim 1.

14. Process for the epoxidation of olefins, comprising:
reacting an olefin with aqueous hydrogen peroxide in the presence of titanium silicalite shaped bodies according to claim 13.

15. Process for the ammoximation of ketones, comprising:
reacting a ketone aqueous hydrogen peroxide and ammonia in the presence of titanium silicalite shaped bodies according to claim 13.

* * * * *

UNITED STATES PATENT AND TRADEMARK OFFICE
CERTIFICATE OF CORRECTION

PATENT NO. : 6,849,570 B2  Page 1 of 1
APPLICATION NO. : 10/204305
DATED : February 1, 2005
INVENTOR(S) : Hasenzahl et al.

It is certified that error appears in the above-identified patent and that said Letters Patent is hereby corrected as shown below:

On the front page at (75) under the heading "Inventors" next to "Steffen Hasenzahl,", replace "Meintal" with --Hanau--.

In claim 3, line 1, delete the phrase "any one of the proceding".

In claim 15, line 3 after the phrase "reacting a ketone" insert the word --with--.

Signed and Sealed this

Twelfth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 6,849,570 B2
APPLICATION NO. : 10/204305
DATED : February 1, 2005
INVENTOR(S) : Hasenzahl et al.

It is certified that error appears in the above-identified patent and that said Letters Patent is hereby corrected as shown below:

In claim 6, line 2, replace the word "mineral" with -- material--.

Signed and Sealed this

Twentieth Day of February, 2007

JON W. DUDAS
*Director of the United States Patent and Trademark Office*